(12) United States Patent
Erez et al.

(10) Patent No.: US 10,864,305 B2
(45) Date of Patent: Dec. 15, 2020

(54) SKIN TREATMENT USING VARIABLE RF

(71) Applicant: Viora Ltd, Netanya (IL)

(72) Inventors: Danny Erez, Kfar Vitkin (IL); Gal Blecher, Kfer Yehezkel (IL)

(73) Assignee: VIORA LTD.

( * ) Notice: Subject to any disclaimer, the term of this patent is extended or adjusted under 35 U.S.C. 154(b) by 93 days.

(21) Appl. No.: 15/658,428

(22) Filed: Jul. 25, 2017

(65) Prior Publication Data
US 2017/0319760 A1 Nov. 9, 2017

Related U.S. Application Data

(63) Continuation of application No. 12/245,374, filed on Oct. 3, 2008, now abandoned.

(51) Int. Cl.
*A61M 1/00* (2006.01)
*A61N 1/40* (2006.01)
*A61B 18/14* (2006.01)
*A61B 18/00* (2006.01)
*A61B 18/12* (2006.01)

(52) U.S. Cl.
CPC ............ *A61M 1/0023* (2013.01); *A61N 1/40* (2013.01); *A61B 2018/00291* (2013.01); *A61B 2018/00452* (2013.01); *A61B 2018/128* (2013.01); *A61B 2018/1467* (2013.01); *A61M 2202/08* (2013.01)

(58) Field of Classification Search
CPC ... A61M 1/0023; A61M 2202/08; A61N 1/40; A61B 2018/1467; A61B 2018/128; A61B 2018/00452; A61B 2018/00291
See application file for complete search history.

(56) References Cited

U.S. PATENT DOCUMENTS

| | | | |
|---|---|---|---|
| 2003/0187488 A1 | 10/2003 | Kreindel et al. | |
| 2007/0088413 A1* | 4/2007 | Weber | A61B 18/14 607/99 |
| 2007/0232962 A1* | 10/2007 | Zumeris | A61H 23/0236 601/2 |
| 2010/0106064 A1* | 4/2010 | Kreindel | A61H 9/0057 601/3 |

OTHER PUBLICATIONS

Meinhardt M, Krebs R, Anders A, Heinrich U, Tronnier H, Wavelength-dependent penetration depths of ultraviolet radiation in human skin, J Biomed Opt. Jul.-Aug. 2008;13(4):044030. doi: 10-1117/1. 2957970; http://www.ncbi.nlm.nih.gOV/pubmed/19021357 (Year: 2008).*

Sadick et al., "Selective Electro-Thermolysis in Aesthetic Medicine: A Review", Lasers in Surgery and Medicine, Wiley-Liss, Inc., 2004, vol. 34, pp. 91-97.

Alster et al., "Nonablative cutaneous remodeling using radiofrequency devices", Clinics in Dermatology, Elsevier Inc., 2007, vol. 25, pp. 487-491.

Alexiades-Armenakas et al., "Unipolar Versus Bipolar Radiofrequency Treatment of Rhytides and Laxity Using a Mobile Painless Delivery Method", Lasers in Surgery and Medicine, Wiley-Liss, Inc., 2008, vol. 40, pp. 446-453.

Brochure/Schedule for IMCAS 2007, International Master Course on Aging Skin, Jan. 10-13, 2007, Paris, France.

\* cited by examiner

*Primary Examiner* — Bradley J Osinski
(74) *Attorney, Agent, or Firm* — Pearl Cohen Zedek Latzer Baratz LLP

(57) ABSTRACT

A skin treatment device used for cellulite treatment, skin tightening or body contouring which combines negative pressure treatment and RF treatment, where the RF treatment uses variable frequencies during a treatment cycle.

13 Claims, 5 Drawing Sheets

SKIN TREATMENT USING VARIABLE RF

CROSS-REFERENCE TO RELATED APPLICATIONS

This application is a continuation of U.S. patent application Ser. No. 12/245,374, filed Oct. 3, 2008, which is hereby incorporated by reference.

FIELD OF THE INVENTION

The present invention relates generally to skin treatment, and particularly to various aesthetic applications such as skin tightening, cellulite treatment and body contouring.

BACKGROUND OF THE INVENTION

The use of negative pressure in skin treatment is known. Negative pressure is used to provide pressure to the soft tissue at a specific location of the skin, and to lift the cellulite structure that is located beneath the skin. The pressure loosens the connection between the cellulite and the skin.

It is also known in the art to use radio frequency (RF) treatment. This treatment is used by selecting an area of tissue and applying electro-magnetic radiation to this area. The electro-magnetic radiation is applied at a radio frequency. The RF treatment dissolves the fatty tissue beneath the selected area of tissue and breaks down the connective bond between the cellulite and the tissue. It is also known to combine RF treatment with negative pressure skin treatment. This increases the amount of cellulite removed as compared with just RF or just negative pressure alone.

Another method of using RF treatment is the use of variable RF frequencies. It has been shown that different RF frequencies are effective at different tissue depths. This may effectively target different tissue depths without the need to apply a large amount of radiation to the skin surface, and possibly further damaging the skin.

SUMMARY OF THE INVENTION

A demonstrative embodiment of the invention may include a system for treating skin. The system may include a negative pressure outlet which may be suitable for the application of negative pressure to an area of skin, a plurality of RF electrodes which may be suitable to emit a plurality of RF energy frequencies to the area of skin and a frequency controller configured to vary the frequency emitted by the RF electrodes. In some embodiments, the negative pressure which may be applied to the area of skin may be from 0.2 to 1 atmosphere. In some embodiments, the frequencies emitted from the RF electrodes may be between 0.8 MHz and 2.4 MHz.

In some embodiments, the controller may vary the RF energy frequencies in a single treatment cycle. The treatment cycle may consist of three pulses, each pulse may last 350 milliseconds. In each treatment cycle, the RF energy frequencies used may include 0.8 MHz, 1.5 MHz and 2.4 MHz. In some embodiments, the single cycle may be divided into three segments, during the first of the three segments lasting 40% of a period of the cycle, an RF energy of 0.8 MHz may be emitted by the electrodes, during the second of the three segments lasting 30% of a period of the cycle, an RF energy of 1.5 MHz may be emitted by the electrodes, and during the third of the three segments lasting 30% of a period of the cycle, an RF energy of 2.4 MHz may be emitted by the electrodes.

In some embodiments, the power of the RF energy may be between 1 to 200 watts.

In some embodiments, the treatment may involve treating subcutaneous adipose tissue.

A demonstrative embodiment of the invention may include a method of skin treatment. The method may include applying a negative pressure during a period to an area of the skin to be treated and emitting during this period onto the skin a plurality of pre-defined RF frequencies, each for pre-defined intervals. The first of the frequencies may be directed to a first layer of adipose tissue in the area, and a second of the frequencies may be directed to adipose tissue in a second layer of the area. In some embodiments, emitting the plurality of pre-defined RF frequencies may include emitting during a first interval RF energy at a frequency of 0.8 MHz, emitting during a second interval RF energy at a frequency of 1.5 MHz, and emitting during a third interval RF energy at a frequency of 2.4 MHz.

In some embodiments, emitting for pre-defined intervals may include emitting the plurality of RF frequencies for intervals of between 100 milliseconds and 300 milliseconds per interval.

In some embodiments, emitting the plurality of RF frequencies may be done at a constant power rate.

In some embodiments, applying negative pressure may include applying negative pressure for pre-defined intervals during the period.

A demonstrative embodiment of the invention may include a method for tightening an area of skin. The method may include selecting a depth of the skin to be tightened, selecting a frequency of RF energy to be applied to the skin and applying the selected frequency of the RF energy to the depth of the skin to be tightened. The frequency selected may correspond to the depth of the skin to be tightened.

In some embodiments, selecting a depth of the skin may include selecting a depth of skin to be tightened of between 0.25 mm and 5 mm, and where selecting a frequency of RF energy to be applied to the skin, may include selecting a frequency of between 0.8 MHz and 2.4 MHz. Some embodiments of the invention may include applying a negative pressure to the area of skin in order to bring the area of skin to be treated into contact with an electrode from which the RF energy is emitted. Some embodiments of the invention may include selecting a power level of said RF energy to be applied to the depth of skin, the power level may be between 1 watt and 200 watts.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
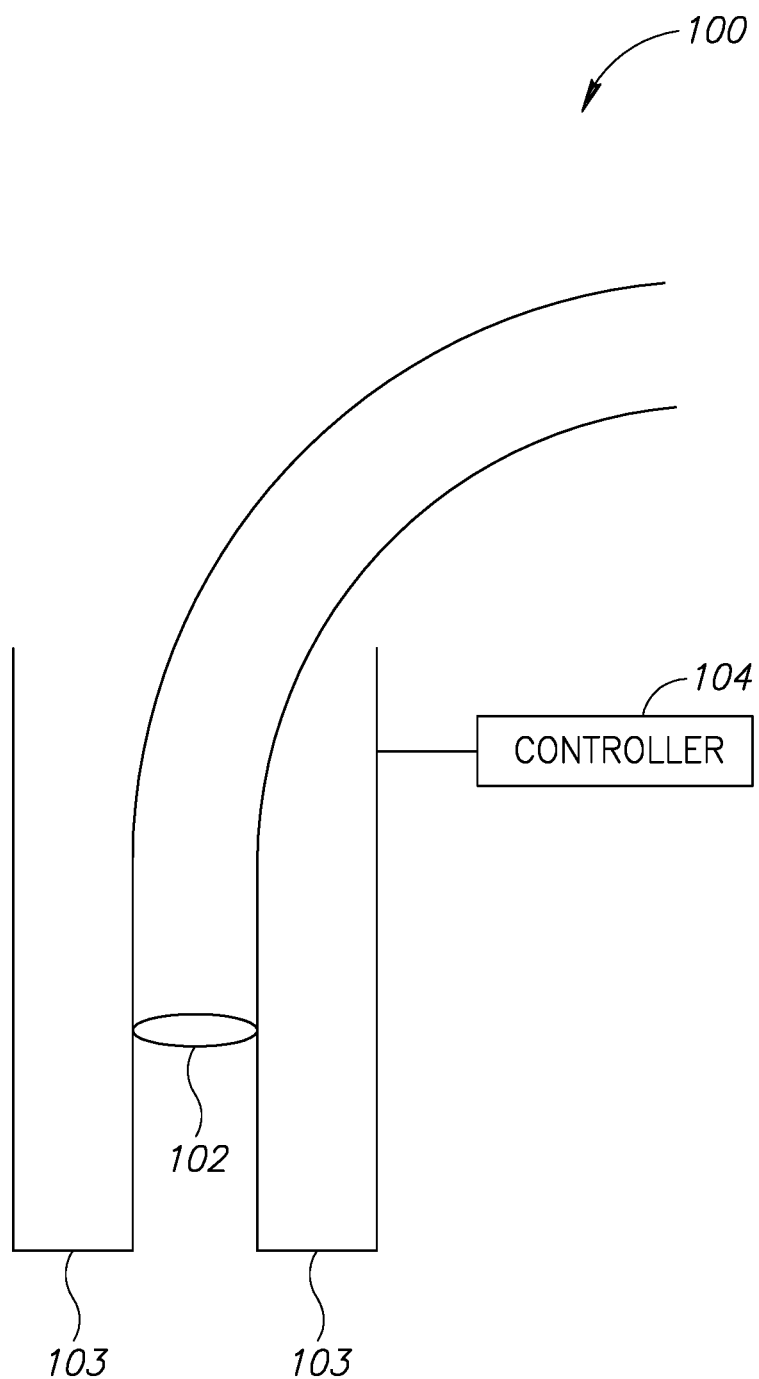
FIG. 1 is a schematic representation of a skin treatment system according to embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of embodiments of the invention. However it will be understood by those of ordinary skill in the art that the embodiments of the invention may be practiced without these specific details. In other instances, well-known methods, procedures, and components have not been described in detail so as not to obscure embodiments of the invention.

The term "skin treatment" as used in this document may refer to treatment of local defects that may be found in the skin. These may include cellulite treatment, skin tightening and body contouring.

Reference is made to FIG. 1, a schematic representation of a skin treatment system according to embodiments of the invention. In some embodiments, a skin treatment device 100 may be used to treat aesthetic conditions such as cellulite and wrinkled skin. In some embodiments, the skin treatment may involve treating subcutaneous adipose tissue. Skin treatment device 100 may include a negative pressure device 102 and a plurality of RF electrodes 103. The device 100 may further be connected to a controller 104. Controller 104 may be used to vary the frequency at which the RF electrodes 103 emit electro-magnetic radiation. The length of time for which electrodes 103 emit this radiation may also be controlled. Controller 104 may also be used to control the suction power of negative pressure device 102. Controller 104 may be used for example to control a number of different functions of device 100.

Device 100 may be placed in contact with a portion of skin that is to be treated. Negative pressure device 102 may be activated by controller 104 to a desirable negative pressure. In some embodiments, the negative pressure may be set for example between 0.2 to 1 atmospheres. Other ranges of negative pressure may be used.

The purpose for negative pressure device 102 may differ depending on its intended use. If for example device 100 is being used for removal of cellulite, negative pressure device 102 may loosen the bond connecting the cellulite structure to the skin. If for example device 100 is being used for skin tightening, negative pressure device 102 may facilitate creation of a better contact between the skin to be treated and electrodes 103.

Electrodes 103 may be activated along with negative pressure device 102 or at other times. To minimize the amount of electro-magnetic energy provided to the skin surface at one time, electrodes 103 may emit various RF frequencies. In some embodiments, the RF frequencies emitted by electrodes 103 may be between 0.8 and 2.4 MHz, though other ranges of frequencies may be used. To determine which frequency may be emitted from electrodes 103, the user may determine the depth of the tissue that is to be treated. To treat deeper layers of tissue, the frequency emitted by electrodes 103 may be increased. In some embodiments of the invention, electrodes 103 may emit the electro-magnetic current for intervals of between 100 to 300 milliseconds, though other periods may be used. In some embodiments, electrodes may emit the current for 350 milliseconds.

In some embodiments, the electrode may be powered at between 1 and 200 watts. If for example, device 100 is used to eliminate cellulite, 50 watts may be used. For skin tightening treatment, 200 watts may be used. Other power ranges are possible. In some embodiments electrodes 103 may provide a constant level of power.

In some embodiments, controller 104 may vary a plurality of pre-defined RF frequencies in a given treatment cycle. Controller 103 may be set so that each treatment cycle includes multiple segments, and each segment lasts for a pre-determined period of time. For example, the frequencies emitted by electrode 103 may be 0.8 MHz, 1.5 MHz and 2.4 MHz and each frequency may set to last 350 milliseconds, though other frequencies and time periods may be used. According to other embodiments of the invention, each of the pre-defined frequencies may be emitted for different periods of time. For example, a single treatment cycle may be divided into three separate segments. During the first segment, a pre-defined frequency may be emitted from electrodes 103 for 40% of the total time cycle. During the second segment, a pre-defined frequency may be emitted from electrodes 103 for 30% of the total time cycle. During the third segment, a pre-defined frequency may be emitted from electrodes 103 for 30% of the total time cycle. According to exemplary embodiments of the invention, the frequency provided by electrodes 103 during the first segment may be 0.8 MHz, the frequency provided by electrodes 103 during the second segment may be 1.5 MHz and the frequency provided by electrodes 103 during the third segment may be 2.4 MHz.

Although not shown in FIG. 1, skin treatment device 100 may also comprise a cooling device to cool the skin surface, and prevent damage to the skin by heat.

Figure 2:
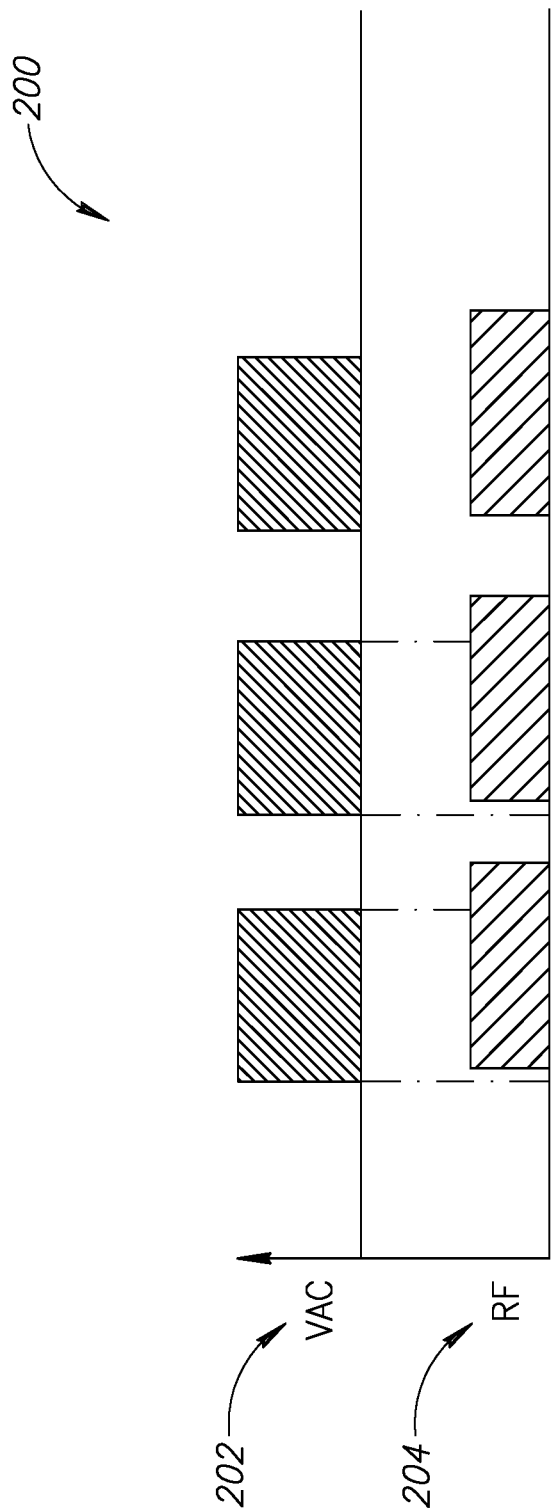
FIG. 2 is an illustration of a method of cellulite treatment according to embodiments of the invention.

Reference is made to FIG. 2 an illustration of a method of cellulite treatment according to embodiments of the invention. As can be seen in FIG. 2 during cellulite treatment 200 the apparatus does not run constantly. Both the negative pressure treatment 202 and the RF treatment 204 may operate in pulses. According to one embodiment of the invention, cellulite treatment 200 may consist of negative pressure treatment 202 and RF treatment 204. Each pulse of negative pressure treatment 202 and RF treatment 204 may be considered to be one cycle. The cycle may start with negative pressure treatment 202. RF treatment 204 may be run soon after the start of negative pressure treatment 202, and may continue after negative pressure treatment 202 is momentarily turned off. After this cycle is completed, a new cycle, again consisting of negative pressure treatment 202 and RF treatment 204 may be repeated. Although FIG. 2 illustrates cellulite treatment 200 having three cycles, the number of cycles required may vary depending on the cellulite treatment required.

Figure 3:
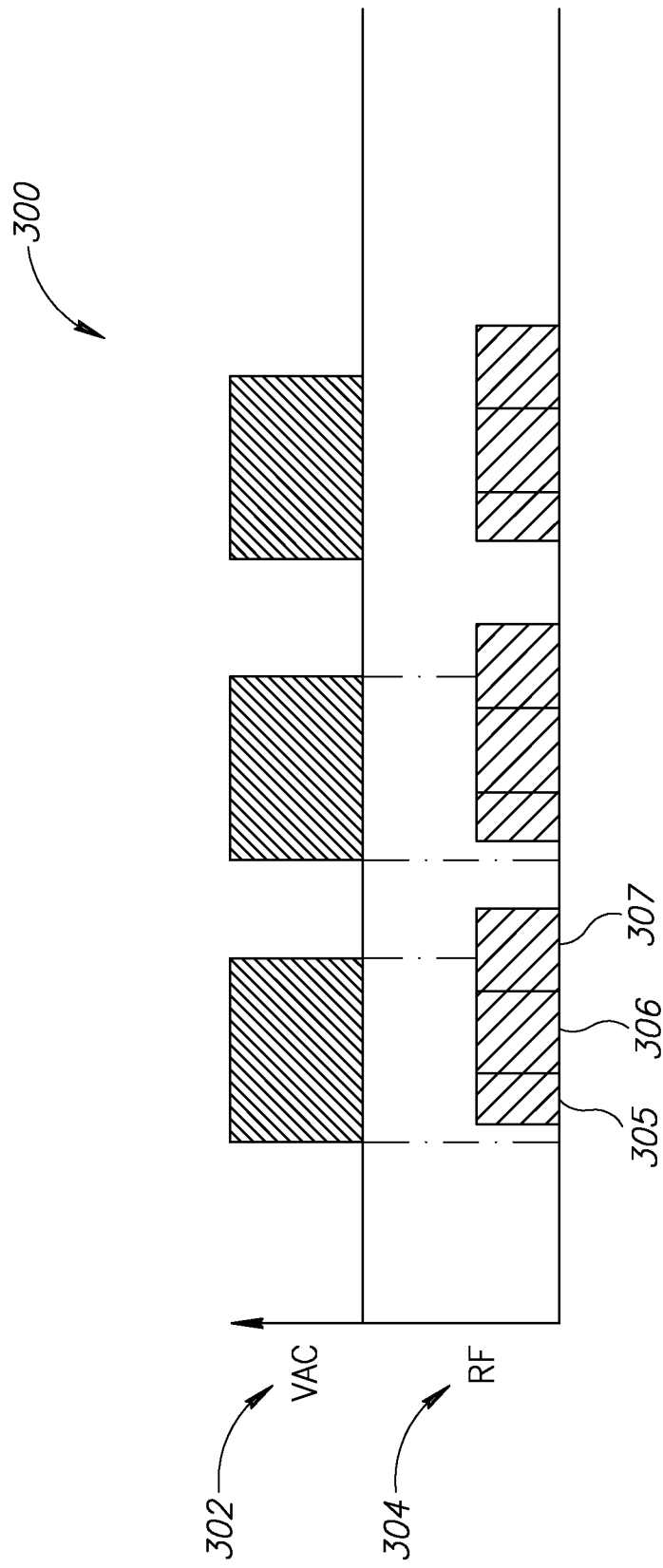
FIG. 3 is an illustration of a method of cellulite treatment using variable RF frequencies according to embodiments of the invention.

Reference is made to FIG. 3 an illustration of a method of cellulite treatment using variable RF frequencies according to embodiments of the invention. As can be seen in FIG. 3 during cellulite treatment 300 the apparatus may not run constantly. Both the negative pressure treatment 302 and the RF treatment 304 may operate in pulses. According to an embodiment of the invention, cellulite treatment 300 may consist of negative pressure treatment 302 and RF treatment 304. Each pulse of negative pressure treatment 302 and RF treatment 304 may be considered to be one cycle. The cycle may start with negative pressure treatment 302. RF treatment 304 may be run soon after the start of negative pressure treatment 302, and may continue after negative pressure treatment 302 is momentarily turned off. RF treatment 304 may consist of using multiple RF frequencies at a constant power rate in one cycle. For example, RF treatment 304 may start with using a first RF frequency 305 of 0.8 MHz, then may use a second RF frequency 306 of 1.5 MHz and then may use a third RF frequency 307 of 2.4 MHz. According to some of the invention, frequencies 305, 306 and 307 may be emitted for the same period of time. According to other embodiments of the invention, frequencies 305, 306 and 307 may last for different periods of time. For example, frequencies 305, 306 and 307 may be emitted for between 100 and 300 milliseconds. After this cycle is completed, a new cycle, again consisting of negative pressure treatment 302 and RF treatment 304 may be repeated. Although FIG. 3 illustrates cellulite treatment 300 having three cycles, the number of cycles required may vary depending on the cellulite treatment required.

Figure 4:
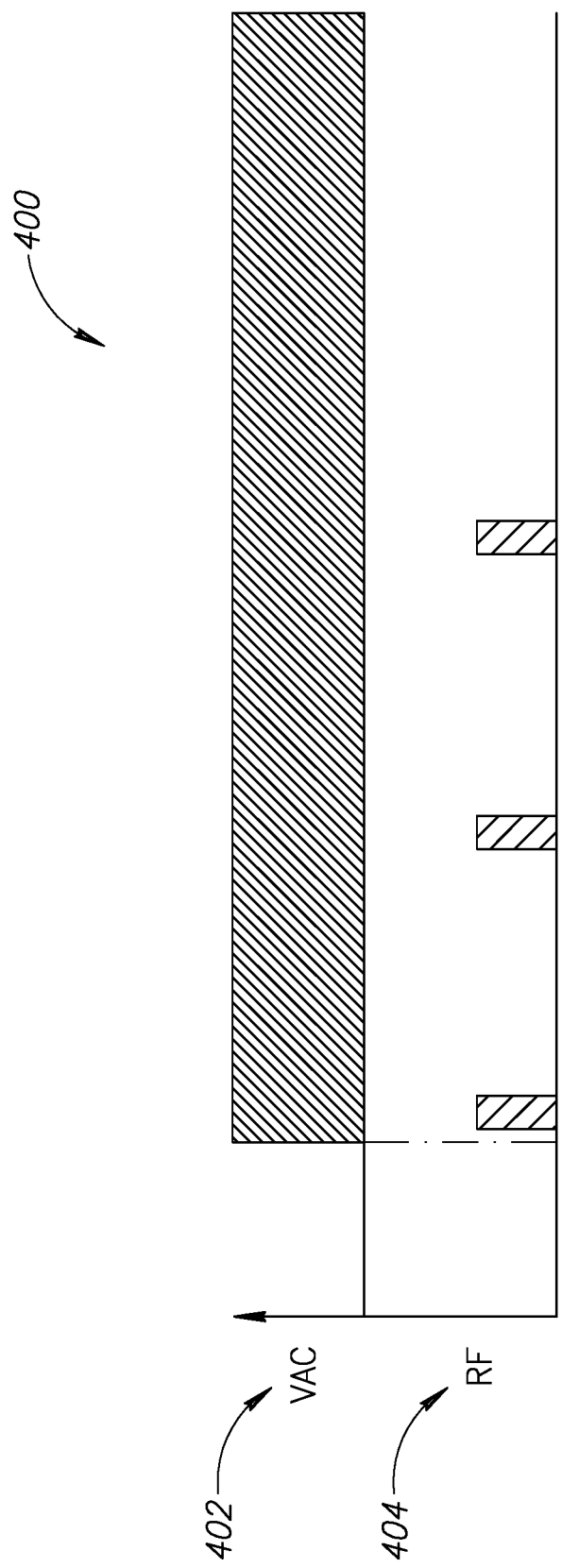
FIG. 4 is an illustration of a method of skin tightening treatment according to embodiments of the invention.

Reference is made to FIG. 4 an illustration of a method of skin tightening according to embodiments of the invention. In order for skin tightening to be effective, the depth of the skin to be tightened may be selected. Since different RF frequencies are effective at different tissue depths, a frequency associated with the selected skin depth may be chosen. Typically, the skin depth to be tightened may for example be between 0.25 and 5 millimeters. As can be seen in FIG. 4 during skin tightening treatment 400, negative pressure 402 may operate constantly during skin tightening treatment 400. RF treatment 404 may operate in pulses. Negative pressure 402 may facilitate a good contact between the skin and the electrodes used in RF treatment 404. Each pulse of RF treatment 404 may be considered to be one cycle. The cycle may start with negative pressure 402. RF treatment 404 may be run soon after the start of negative pressure 402, and may continue for a pre-determined amount of time. According to some embodiments, the frequency of the RD may be between 0.8 and 2.4 MHz. After this cycle is completed, a new cycle, may be repeated. Although FIG. 4 illustrates skin tightening treatment 400 having three cycles, the number of cycles required may vary depending on the skin tightening treatment required.

Figure 5:
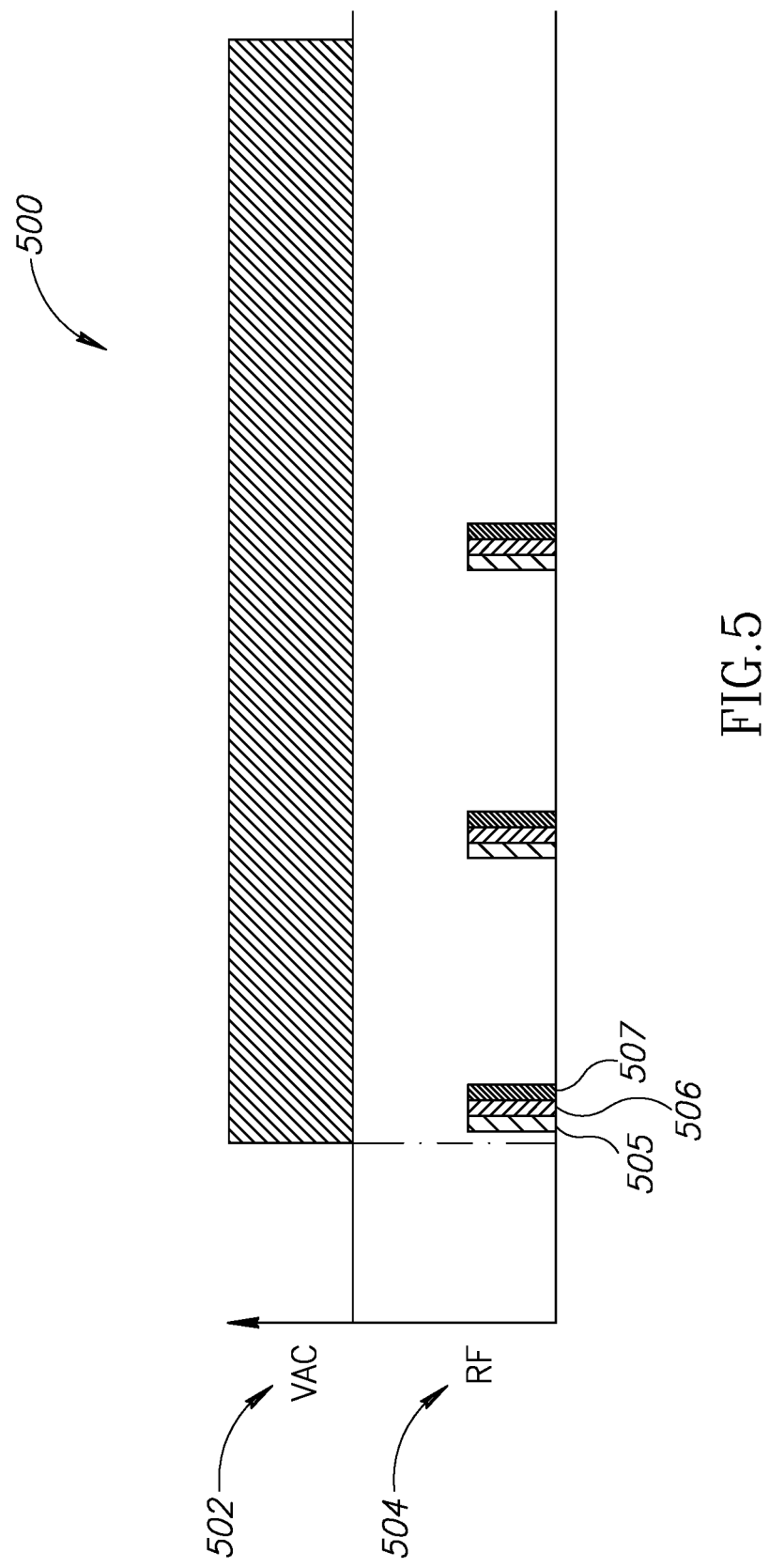
FIG. 5 is an illustration of a method of skin tightening treatment using variable RF frequencies according to embodiments of the invention.

Reference is made to FIG. 5 an illustration of a method of skin tightening using variable RF frequencies according to embodiments of the invention. As can be seen in FIG. 5 during skin tightening treatment 500, negative pressure 502 may operate constantly during skin tightening treatment 500. RF treatment 504 may operate in pulses. One of the purposes of negative pressure 502 is so that the electrodes used in RF treatment 504 may be provided with good contact with the skin to be treated. A treatment cycle may start with negative pressure 502. RF treatment 504 may be run soon after the start of negative pressure 502, and may continue for a pre-determined amount of time. RF treatment 504 may consist of using multiple RF frequencies in one cycle. For example, RF treatment 504 may start with using a first RF frequency 505 of 0.8 MHz, then may use a second RF frequency 506 of 1.5 MHz and then may use a third RF frequency 507 of 2.4 MHz. According to some of the invention, frequencies 505, 506 and 507 may be emitted for the same period of time. According to other embodiments of the invention, frequencies 505, 506 and 507 may last for different periods of time. After this cycle is completed, a new cycle, may be repeated. Although FIG. 5 illustrates skin tightening treatment 500 having three cycles, the number of cycles required may vary depending on the skin tightening treatment required.

While certain features of the invention have been illustrated and described herein, many modifications, substitutions, changes and equivalents will now occur to those of ordinary skilled in the art. It is, therefore, to be understood that the appended claims are intended to cover all such modifications and changes as fall within the spirit of the invention.

What is claimed is:

1. A system for treating skin, comprising:
a negative pressure outlet suitable for application of negative pressure to an area of skin;
two electrodes configured to emit a plurality of RF energy frequencies to said area of skin; and
a controller configured to:
receive a selection of a skin treatment type;
apply, during a single treatment cycle, two or more RF frequencies of said RF energy frequencies by a single electrode of the two electrodes, wherein the frequencies are selected according to the skin treatment type; and
apply, during the treatment cycle, an amount of negative pressure by said negative pressure outlet, the amount is determined according to the skin treatment type,
wherein each treatment cycle comprises a pulse of said two or more RF frequencies.

2. The system according to claim 1 wherein said negative pressure is from 0.2 to 1 atmosphere.

3. The system as in claim 1, wherein said frequencies are between 0.8 MHz and 2.4 MHz.

4. The system as in claim 1, wherein said treatment cycle comprises three pulses of 350 milliseconds each.

5. The system as in claim 1, wherein said plurality RF energy frequencies in said treatment cycle include 0.8 MHz, 1.5 MHz and 2.4 MHz.

6. The system as in claim 1, wherein said treatment cycle is divided into three segments, during a first of said three segments lasting 40% of a period of said cycle, RF energy of 0.8 MHz is emitted by said electrodes, during a second of said three segments lasting 30% of a period of said cycle, RF energy of 1.5 MHz is emitted by said electrodes, and during a third of said three segments lasting 30% of a period of said cycle, RF energy of 2.4 MHz is emitted by said electrodes.

7. The system according to claim 1, wherein a power of the RF energy is between 1 to 200 watts.

8. The system according to claim 1, wherein the treatment involves treating subcutaneous adipose tissue.

9. A method of skin treatment, comprising:
receiving a selection of a skin treatment type;
applying during a single treatment cycle two or more RF frequencies by a single electrode of two electrodes included in a system for treating skin, wherein the frequencies are selected according to the skin treatment type, wherein each one of said two electrodes is configured to emit a plurality of RF energy frequencies to an area of skin; and
applying, during the treatment cycle, an amount of negative pressure by a negative pressure outlet, the amount is determined according to the skin treatment type, wherein said negative pressure outlet is suitable for application of negative pressure to said area of skin,
wherein each treatment cycle comprises a pulse of said two or more RF frequencies.

10. The method as in claim 9, wherein said applying said one or more RF frequencies comprises emitting during a first interval RF energy at a frequency of 0.8 MHz, emitting during a second interval RF energy at a frequency of 1.5 MHz, and emitting during a third interval RF energy at a frequency of 2.4 MHz.

11. The method as in claim 9, wherein said applying said one or more RF frequencies is at intervals of between 100 milliseconds and 300 milliseconds per interval.

12. The method as in claim 9, further comprising applying said plurality of RF frequencies at a constant power rate.

13. The method as in claim 9, wherein said applying negative pressure comprises applying negative pressure for pre-defined intervals during said period.

* * * * *